| United States Patent [19] | [11] Patent Number: 5,017,617 |
|---|---|
| Kihara et al. | [45] Date of Patent: May 21, 1991 |

[54] DISINFECTANT COMPOSITION FOR MEDICAL USE

[75] Inventors: Koji Kihara, Yamatokoriyama; Taro Furuta, Kashiwara, both of Japan

[73] Assignee: Saraya Kabushiki Kaisha, Osaka, Japan

[21] Appl. No.: 322,767

[22] Filed: Mar. 13, 1989

[30] Foreign Application Priority Data

Nov. 22, 1988 [JP] Japan ................................. 63-294962

[51] Int. Cl.$^5$ ..................... A01N 31/00; A01N 37/12; A01N 37/52; A01N 43/40
[52] U.S. Cl. .................................... 514/635; 514/358; 514/642; 514/643; 514/724
[58] Field of Search ............... 514/358, 642, 643, 635, 514/724

[56] References Cited

U.S. PATENT DOCUMENTS

| Re. 32,300 | 12/1986 | Gorman et al. | 514/635 |
| 2,446,796 | 8/1948 | Campen et al. | 514/358 |
| 3,932,655 | 1/1976 | Conn | 514/643 |

FOREIGN PATENT DOCUMENTS 519557 12/1985 Fed. Rep. of Germany ...... 514/643

OTHER PUBLICATIONS

K. Kihara et al. J. Antibact. Antifung, Agents, vol. 14, No. 12, 1986, pp. 597–604.
K. Kihara et al., The 13th Nenji Taikai Yoshishu, May 1986, pp. 86–87.

*Primary Examiner*—Allen J. Robinson
*Attorney, Agent, or Firm*—Irell & Manella

[57] ABSTRACT

A disinfectant composition for medical use is provided that has satisfactory bactericidal effects, and that rarely causes skin damage even when used frequently. The composition comprises ethanol used for disinfection, a bactericidal agent, and an emollient, wherein said bactericidal agent is at least one selected from the group consisting of chlorhexidine digluconate, alkylpyridinium salts, and quaternary ammonium salts, and said emollient is at least one selected from the group consisting of diesters of dibasic acid, triesters of citric acid, triesters of phosphoric acid, polyoxyethylene glyceride of higher fatty acid, and polyglycerol.

2 Claims, 3 Drawing Sheets

FIG. 1

DISINFECTANT COMPOSITION FOR MEDICAL USE

BACKGROUND OF THE INVENTION

1. Field of the invention:

This invention relates to a disinfectant composition for medical use that is suitable for disinfection of the hands.

2. Description of the prior art:

Washbasins containing an aqueous solution of a disinfectant are provided in the nursing stations of hospitals, the entrances of hospital wards, the entrance of intensive care units, and elsewhere. For disinfection of the hands, both hands are immersed in the solution. However, a number of problems have recently been pointed out with the method that uses such basins, some of which include (1) the danger that the basin itself will become a source of infection by a variety of microorganisms if the concentration of the drug falls below a certain level, (2) the appearance of drug-resistant strains of microorganisms if the same disinfectant is used for a long period of time, and (3) the danger of recontamination after immersion from hand towels and the like. For that reason, suitable bactericidal agents such as those in ethanol solution that provide disinfection with rapid drying have been investigated.

As rapid-drying disinfectant solutions, there are ethanol solutions containing chlorhexidine digluconate, ethanol solutions containing benzalkonium chloride, etc. These disinfectant solutions are prepared by the addition of 0.1-0.5% (wt/v) of chlorhexidine digluconate or benzalkonium chloride to ethanol for disinfection (Japanese Pharmacopoeia, 76.9 to 81.4% (v/v) of ethanol in water). Because these disinfectant solutions are rapid drying and have the additional bactericidal effect of ethanol, and because chlorhexidine digluconate or benzalkonium chloride are contained therein, they can be used for the disinfection of the skin before surgery, medical devices in cases of emergency, etc. However, because contact of the skin to the ethanol solvent causes denaturation of structural proteins of the skin such as keratin, injury of the skin such as irritation or roughening may occur. For that reason, such solutions are not generally used for the frequent disinfection of the hands.

The inventors of this invention thought of the possibility of preventing skin damage by the addition of an emollient that protects the skin to this kind of disinfectant solution with ethanol as its main solvent. However, it is known that the bactericidal activity of chlorhexidine digluconate and benzalkonium chloride decreases in the presence of other substances. For example, in the presence of various substances such as serum [Journal of Infectious Diseases 53, 292 (1979)], polysaccharides [J. Periodont. Res. 8, Suppl. 12, 61 (1973)], non-ionic surfactants (Medical Journal of Okayama University 91, 251 (1979)], powdered milk, dried bovine serum, fish powder, and other organic substances [J. Appl. Bacterial., 54, 243 (1983)], the bactericidal activity of these compounds decreases. Most emollients used in cosmetics and the like are non-ionic surfactants or higher alcohols, so it is likely that when they are added, the bactericidal activity of chlorhexidine digluconate and benzalkonium chloride would decrease. In this way, an disinfectant composition for medical use that is rapid-drying and has satisfactory bactericidal activity but that does not damage the skin is not presently available.

SUMMARY OF THE INVENTION

The disinfectant composition for medical use, which overcomes the above-discussed and numerous other disadvantages and deficiencies of the prior art, comprises ethanol used for disinfection, a bactericidal agent, and an emollient, wherein said bactericidal agent is at least one selected from the group consisting of chlorhexidine digluconate, alkylpyridinium salts, and quaternary ammonium salts, and said emollient is at least one selected from the group consisting of diesters of dibasic acid, triesters of citric acid, triesters of phosphoric acid, polyoxyethylene glyceride of higher fatty acid, and polyglycerol.

In a preferred embodiment, the ethanol used for disinfection is an aqueous solution of ethanol ranging in concentration from 50 to 95% (v/v).

In a preferred embodiment, the bactericidal agents are contained at a concentration of from 0.01 to 0.5% (wt/v).

In a preferred embodiment, the emollient is contained at a concentration of from 0.1 to 1.0% (wt/v).

Thus, the invention described herein makes possible the objectives of (1) providing a disinfectant composition for medical use that has satisfactory bactericidal effects, that is rapid-drying, and that rarely causes skin damage even when used frequently; (2) providing a disinfectant composition for medical use that comprises an ethanol solution containing a bactericidal agent and an emollient; (3) providing a disinfectant composition for medical use that contains an emollient capable of enhancing the effects of the bactericidal agent; and (4) providing a disinfectant composition with a wide range of medical uses such as the disinfection of the hands in hospital settings, the disinfection of the skin before surgery, the disinfection of medical appliances, and the like.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

The inventors of this application have found emollients capable of enhancing the bactericidal activity of various bactericidal agents during a search for emollients that would not lower the bactericidal activity of various bactericidal agents, and this invention was completed on the basis of this novel finding. The disinfectant composition of this invention for medical use is an disinfectant composition with a wide range of possible applications in the field of medicine, including disinfection of the hands, disinfection of the skin before surgery, disinfection of medical appliances, and the like. The ethanol for use in disinfection that is contained in the disinfectant composition of this invention may be any ethanol solution that has bactericidal effects and that can dissolve an emollient. Generally, an aqueous solution of ethanol of 50-95% (v/v), and preferably 65-85% (v/v), is used. For example, it is suitable to use "ethanol for disinfection" listed in the Japanese Pharmacopoeia.

The alkylpyridinium salt that is one of the bactericidal agents that can be contained in the disinfectant composition for medical use of this invention is of the formula:

(I)

wherein $R^1$ is alkyl containing 8 to 20, and preferably 14 to 18 carbon atoms; and X is halogen. The disinfectant composition can contain a mixture of different alkylpyridinium salts. A representative example of an alkylpyridinium salt is cetylpyridinium chloride.

The quaternary ammonium salt that is one of the bactericidal agents that can be included in the composition is of the following formula II or III:

(II)

(III)

In formula II, $R^2$ is alkyl containing 8 to 20 carbon atoms, $R^3$ is benzyl, or alkyl containing 1 to 20 carbon atoms, and X is halogen, with the proviso that when $R^3$ is alkyl, the total number of carbon atoms contained in $R^2$ and $R^3$ is equal to or less than 28. The disinfectant composition can contain a mixture of different quaternary ammonium salts. In formula III, $R^4$ is alkyl containing 2 to 10 carbon atoms, $R^5$ is methyl or benzyl, X is halogen, and m is equal to 2 or 3. Typical quaternary ammonium salts include cetyltrimethylammonium chloride, dodecyldimethylbenzylammonium chloride, benzalkonium chloride, didecyldimethylammonium chloride and benzethonium chloride. These bactericidal agents are contained in the composition at the proportion of 0.01-0.5% (wt/v), and preferably 0.1-0.5% (wt/v).

The diester of dibasic acid that can be used as an emollient in the disinfectant composition of this invention is a compound formed from one molecule of an aromatic or aliphatic dibasic acid containing 1-8 methylene groups and two molecules of alcohol containing 4-6 carbon atoms. The diester of dibasic acid has the following formula II, with an ester linkage.

(IV)

wherein $R^6$ is alkyl containing 4 to 6 carbon atoms, and $R^7$ is phenylene or polymethylene of the formula $-(CH_2)_n-$, and n is an integer of from 2 to 8. The alkyl group $R^6$ can be either a straight chain or a branched chain. For example, $R^6$ can be an n-butyl group, isobutyl group, or tert-butyl group. The disinfectant composition can contain a mixture of different diesters of dibasic acids. Diesters of dibasic acids with formula IV and that are widely used in the field of cosmetics as emollients include dibutyl adipate, diisobutyl adipate, dihexyl adipate, dibutyl sebacate, dibutyl phthalate, and mixtures thereof. These compounds are preferably used in the composition of this invention.

The triester of citric acid listed above as an emollient is a compound with the following formula V, and is a condensation product formed from one molecule of citric acid, and three molecules of alcohol containing 4-6 carbon atoms.

(V)

wherein $R^8$ is alkyl containing 4 to 6 carbon atoms. The disinfectant composition can contain a mixture of different triesters of citric acid. A preferred example of a triester of citric acid that is widely used as an emollient in the field of cosmetics and that is appropriate for use in the composition of this invention is tributyl citrate.

The triester of phosphoric acid listed above as an emollient is a compound with the following formula VI, and is a condensation product formed from one molecule of phosphoric acid and three molecules of alcohol containing 4-6 carbon atoms.

(VI)

wherein $R^9$ is alkyl containing 4 to 6 carbon atoms. The disinfectant composition can contain a mixture of different triesters of phosphoric acid. A preferred examples of a triester of phosphoric acid is tributyl phosphate.

The polyoxyethylene glyceride of higher fatty acid listed above as an emollient has a fatty acid with 8-18 carbon atoms as an constituent. The polyoxyethylene glyceride of higher fatty acid of formula VII is formed from one molecule of the fatty acid, one molecule of glycerin, and 1-30 molecules of ethylene oxides.

(VII)

wherein $R^{10}$ is alkyl containing 7 to 17 carbon atoms and n is an integer of from 1 to 30. The disinfectant composition can contain a mixture of different polyoxyethylene glycerides of higher fatty acid. For example, if a mixture of fatty acids obtained from coconut oil is used that contains fatty acids each having 8-18 carbon atoms and that has lauric acid as its main component, a mixture of compounds of formula VII in which the carbon number is different for $R^{10}$ is obtained.

Of emollients, polyglycerols are condensation products of 2-15 glycerins. A mixture of polyglycerols with different numbers of glycerins can be used.

The emollients used in this invention act to soften skin, and act to supplement skin oils, so as to inhibit skin damage such as skin irritation and roughing caused by the ethanol. At the same time, the emollients enhance the bactericidal activity of the bactericidal agent contained in the composition. The mechanism of the enhancement is still not clearly understood, but it seems that these emollients and the bactericidal agents have mutual and additive effects as the bactericidal agent acts on bacterial cells. The emollient is contained in the composition in the proportion of 0.10–1.0% (wt/v), and preferably at 0.2–0.4% (wt/v). If the amount of the emollient is too small, the effects mentioned above are not obtained. If the amount is too large, the emollient will remain on the skin, giving rise to stickiness.

The solution for medical use according to this invention can be formulated, for example, by the dissolution of such a bactericidal agent and such an emollient in an 80% (v/v) aqueous solution of ethanol, the solution of ethanol being ethanol for disinfection listed in the Japanese Pharmacopoeia. The bactericidal effects of both the bactericidal agent and the ethanol are obtained when the hands are immersed in this solution, and the emollient enhances the bactericidal effects of the bactericidal agent. Of course, the emollient is also effective in preventing skin roughness, as well. This disinfectant solution is rapid-drying, so there is no need for hand towels or the like to be used, and the danger of recontamination from such hand towels is eliminated. Because the emollient and the bactericidal agent remain on the skin surface after the solvents (i.e., the ethanol and water) have vaporized, a satisfactory bactericidal effect is obtained. The composition of this invention can be used for disinfection of the hands, disinfection of medical devices and the like, and a wide variety of other medical uses.

EXAMPLE

Below, the invention will be explained with reference to examples.

EXAMPLE 1

Thirteen kinds of emollients that could be dissolved in an 80% (v/v) aqueous solution of ethanol containing chlorhexidine digluconate were selected (Nos. 1–13 in Table 1). The effects of these emollients on the bactericidal activity of chlorhexidine digluconate were examined.

To an 80% (v/v) aqueous solution of ethanol that contained 0.2% (wt/v) chlorhexidine digluconate, one of the 13 kinds of emollients listed as Nos. 1–13 in Table 1 was added at the proportion of 0.2% (wt/v). Thus, 13 kinds of sample solutions were obtained. Separately, instead of an emollient, serum was added at the proportion of 0.2% (wt/v), and the effects of this sample solution (No. 14) were also examined.

A glass cylinder (diameter, 25 mm; height, 65 mm) was placed in the bottom of a 100-ml beaker, and chromatography paper (Toyo Roshi No. 50; 20×25 mm) was placed on the upper end of the cylinder. Then 50 µl of one of the sample solutions listed above was dropped onto the center of the paper; the beaker was covered with a glass lid (diameter, 75 mm) and the paper was allowed to dry for 2 hours. Then, 20 µl of a suspension of *Staphylococcus aureus* ATCC No. 25923 that had been cultured in nutrient broth for 16 hours at 37° C. was dropped onto the area of the dried sample in the middle of the filter paper. The beaker was covered and was allowed to stand at room temperature for 10 minutes. The filter paper was placed in a bottle that contained 20 g of sterilized glass beads (bead diameter, 3 mm) and 50 ml of sampling solution. The bottle was shaken vigorously for 45 seconds. The number of viable bacteria in this sampling solution was measured by the agar dilution method. The sampling solution used was a 0.3% aqueous solution of cocamide ether sulfate. The cocamide ether sulfate inactivated the chlorhexidine digluconate that was eluted into the sampling solution from the filter paper. The experiments with the samples containing different emollients, the sample containing serum, and the control sample not containing emollients were repeated a total of three times for each sample. Measurement was also done of filter paper that was not treated with drops of the sample solutions. The numbers of viable bacteria in 500 µl of the sampling solution are shown in Table 1, and the results of variance analysis of logarithms of the numbers of viable bacteria per 1 µl of the sampling solution are given in FIG. 1.

TABLE 1

| Emollient or additive | Abbreviation | Number of viable bacteria (Number of colonies/500 µl of sampling solution) | | |
|---|---|---|---|---|
| | | (No. 1) | (No. 2) | (No. 3) |
| (1) Hexyl laurate | HL | $98 \times 10^2$ | $142 \times 10^2$ | $90 \times 10^2$ |
| (2) Polyoxyethylene (7) glyceryl monococoate | GC | $124 \times 10$ | $135 \times 10$ | $42 \times 10$ |
| (3) Propyleneglycol dicaprylate | PDC | $49 \times 10^2$ | $74 \times 10^2$ | $117 \times 10^2$ |
| (4) Caprylic/capric triglyceride | CCTG | $131 \times 10^2$ | $68 \times 10^2$ | $75 \times 10^2$ |
| (5) 2-Octyldodecanol | OD | $50 \times 10^2$ | $93 \times 10^2$ | $55 \times 10^2$ |
| (6) Diisobutyl adipate | DIBA | $84 \times 10$ | $154 \times 10$ | 40 |
| (7) Glyceryl tri (2-ethylhexanoate) | GTEH | $211 \times 10$ | $30 \times 10^2$ | $50 \times 10^2$ |
| (8) Isopropyl myristate | IPM | $47 \times 10^2$ | $73 \times 10^2$ | $69 \times 10^2$ |
| (9) Isopropyl palmitate | IPP | $80 \times 10^2$ | $71 \times 10^2$ | $70 \times 10^2$ |
| (10) Isopropyl isostearate | IPIS | $81 \times 10^2$ | $60 \times 10^2$ | $39 \times 10^2$ |
| (11) Cetyl lactate | CL | $139 \times 10$ | $49 \times 10^2$ | $65 \times 10^2$ |
| (12) Diisopropyl adipate | DIPA | $34 \times 10^2$ | $85 \times 10$ | $43 \times 10^2$ |
| (13) Polyglycerol (degree of condensation, 5) | PG | $28 \times 10^2$ | $206 \times 10$ | $30 \times 10^2$ |
| (14) Serum | S | $80 \times 10^3$ | $58 \times 10^3$ | $65 \times 10^3$ |
| (15) Control (no emollient) | R | $64 \times 10^2$ | $142 \times 10^2$ | $92 \times 10^2$ |
| (16) Untreated | B | $98 \times 10^3$ | $102 \times 10^3$ | $83 \times 10^3$ |

Figure 1:
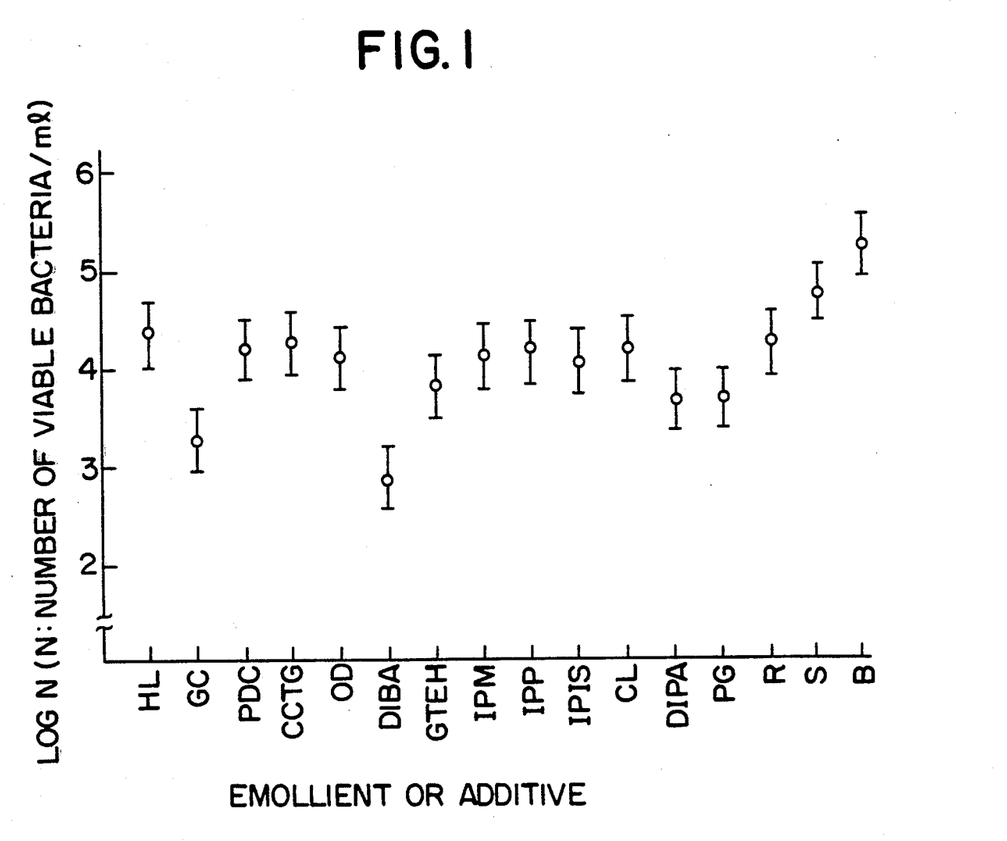
FIG. 1 is a graph showing the results of measurements of the bactericidal activity of chlorhexidine digluconate toward Staphylococcus aureus in the presence of various kinds of emollients or additives.

Table 1 and FIG. 1 show that when serum was added to an 80% (v/v) aqueous solution of ethanol containing chlorhexidine digluconate, the bactericidal activity of the chlorhexidine digluconate decreased, but that when any of the 13 emollients listed was added, the bacterial activity of the chlorhexidine digluconate did not decrease. Also, FIG. 1 shows that the number of viable bacteria expressed logarithmically was $2 \times 10^4$ with the control sample, to which an emollient was not added; when diisopropyl adipate (DIPA) or polyglycerol (PG) was added, the number was $5 \times 10^3$; when polyoxyethylene(7) glyceryl monococoate (GC; 7 molecules of ethylene oxide are incorporated) was added, the number was $2 \times 10^3$; and when diisobutyl adipate (DIBA) was added, the number was $7 \times 10^2$. Thus, compared to the results obtained when an emollient was not added, there were significantly fewer viable bacteria when GC or DIBA was added (both, $p<0.01$) and when DIPA or PG was added (both, $p<0.05$). That is, the addition of these emollients caused a decrease to 1/10–1/100 in the number of viable bacteria. This shows that the emollients used in this invention enhanced the bactericidal activity of chlorhexidine digluconate.

In a separate experiment, measurement was made in the same way with an 80% (v/v) aqueous solution of ethanol that contained 0.4% (wt/v) chlorhexidine digluconate and that did not contain any emollient. The results concerning bactericidal activity were almost the same as those obtained above when the emollient was added to the concentration of 0.2% (wt/v).

EXAMPLE 2

Figure 2:
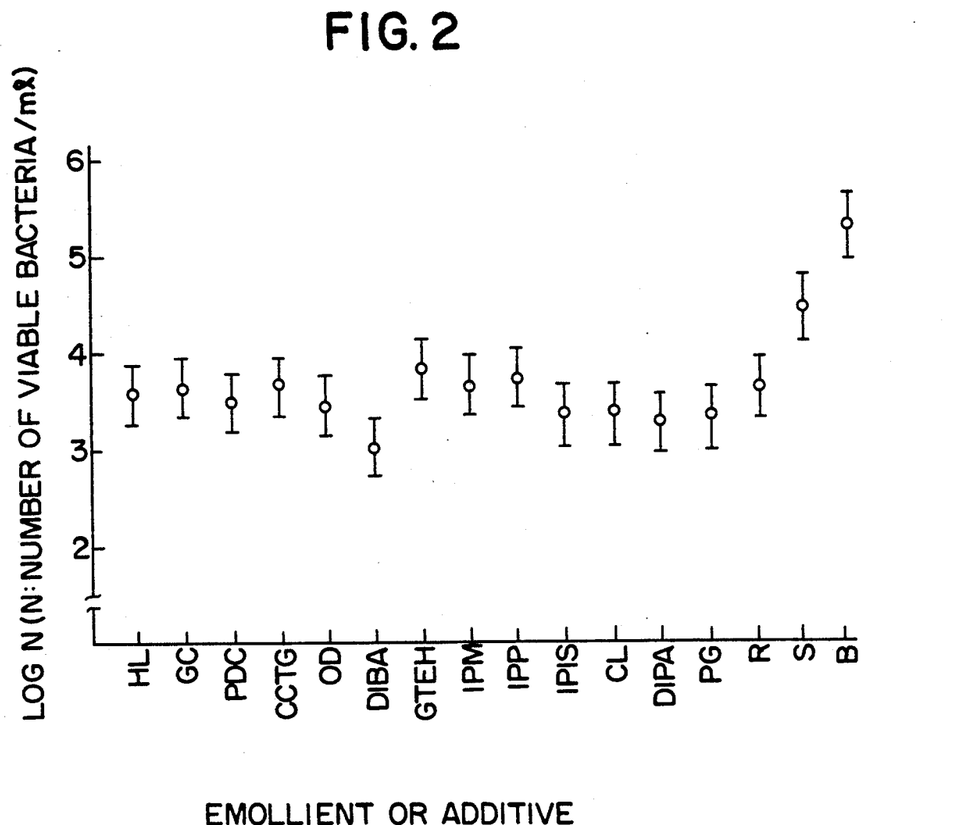
FIGS. 2 and 3 are graphs showing the results of the same kind of measurements with Pseudomonas aeruginosa and Serratia marcescens, respectively, instead of Staphylococcus aureus.

The procedure of Example 1 was repeated except that *Pseudomonas aeruginosa* was used instead of *Staphylococcus aureus*. Results are given in FIG. 2. FIG. 2 shows that the bactericidal activity of chlorhexidine digluconate against *P. aeruginosa* was not decreased by the presence of any of these emollients. Also, the DIBA used in this invention enhanced the bactericidal activity of the chlorhexidine digluconate, resulting in only $1 \times 10^3$ viable bacteria, which was significantly fewer ($p<0.01$) than the $4 \times 10^3$ viable bacteria recovered when an emollient was not added.

EXAMPLE 3

Figure 3:
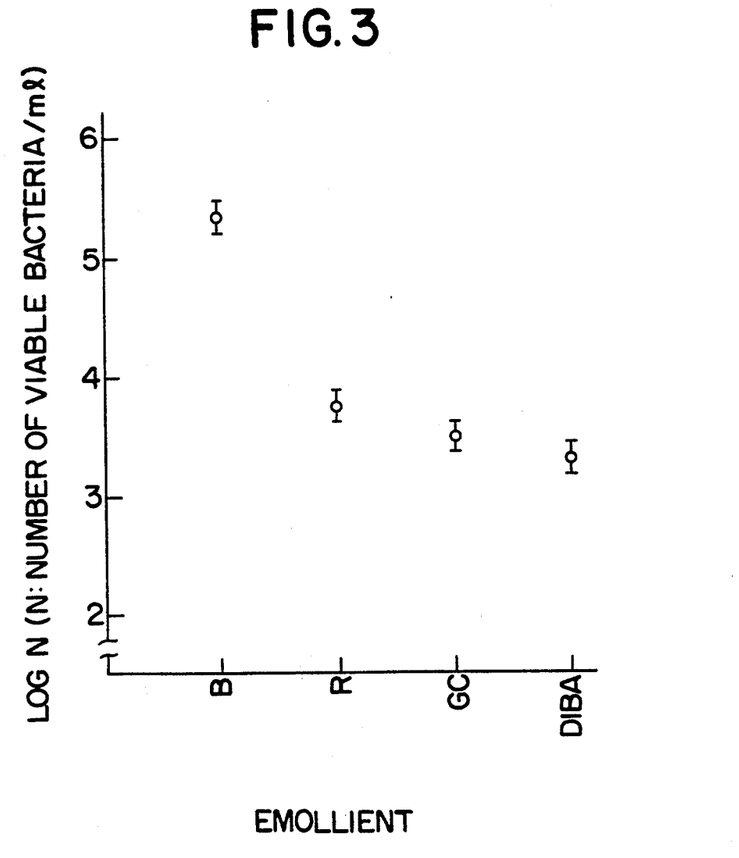

The procedure of Example 1 was repeated, except that *Serratia marcescens* was used instead of *Staphylococcus aureus* and, GC or DIBA was used as emollient. Results are given in FIG. 3. FIG. 3 shows that compared to the $5 \times 10^3$ viable bacteria collected when the control sample (R) without emollient was used, there were significantly fewer viable bacteria when GC was added ($3 \times 10^3$ viable bacteria) or when DIBA was added ($2 \times 10^3$ viable bacteria; both $p<0.01$). Thus, both the GC and the DIBA used in this invention enhance the bactericidal activity of chlorhexidine digluconate against *Serratia marcescens*.

EXAMPLE 4

The effects of the addition of two emollients to one sample were examined. As shown in Table 2, both GC and DIPA were added to an 80% (v/v) aqueous solution of ethanol that contained 0.2% (wt/v) chlorhexidine digluconate at various concentrations so that 16 kinds of sample solutions were obtained. The effects of the 16 sample solutions with different emollient concentrations were tested by the methods of Example 1. Each experiment was repeated for a total of 2 times. The results are shown in Table 2.

TABLE 2

| | | Number of viable bacteria (Number of colonies/500 μl of sampling solution) | | | |
|---|---|---|---|---|---|
| | | Concentration of GC (%, wt/v) | | | |
| | | 0 | 0.1 | 0.2 | 0.4 |
| Concentration of DIPA % (wt/v) | 0 | $119 \times 10^2$ | $28 \times 10^3$ | $161 \times 10^2$ | $68 \times 10^2$ |
| | | $171 \times 10^2$ | $102 \times 10^2$ | $43 \times 10^2$ | $163 \times 10$ |
| | 0.1 | $32 \times 10^3$ | $196 \times 10^2$ | $130 \times 10^2$ | $99 \times 10^2$ |
| | | $140 \times 10^2$ | $49 \times 10^2$ | $31 \times 10^2$ | $97 \times 10$ |
| | 0.2 | $185 \times 10^2$ | $55 \times 10^2$ | $124 \times 10^2$ | $48 \times 10^2$ |

TABLE 2-continued

| | Number of viable bacteria (Number of colonies/500 μl of sampling solution) | | | |
|---|---|---|---|---|
| | Concentration of GC (%, wt/v) | | | |
| | 0 | 0.1 | 0.2 | 0.4 |
| 0.4 | $44 \times 10^2$ | $198 \times 10$ | $178 \times 10$ | $97 \times 10$ |
| | $69 \times 10^2$ | $29 \times 10^2$ | $79 \times 10$ | $133 \times 10$ |
| | $43 \times 10$ | $20 \times 10$ | 26 | 38 |

Table 2 shows that within the range of concentrations tested, GC and DIPA had additive effects in enhancing the bactericidal activity of chlorhexidine digluconate.

EXAMPLE 5

In an 80% (v/v) aqueous solution of ethanol, GC was dissolved to the concentration of 0.2% (wt/v). This was used as the sample solution, and the methods of Example 1 were used to calculate the number of viable cells of *Staphylococcus aureus* in 500 μl of sampling solution. The same experiment was repeated with DIBA, DIPA, or PG used instead of the GC. The results are shown in Table 3.

TABLE 3

| | Number of viable bacteria (Number of colonies/500 μl of sampling solution) | | |
|---|---|---|---|
| Emollient | (No. 1) | (No. 2) | (No. 3) |
| Polyoxyethylene (7) glyceryl monococoate | $147 \times 10^3$ | $143 \times 10^3$ | $149 \times 10^3$ |
| Diisobutyl adipate | $114 \times 10^3$ | $139 \times 10^3$ | $122 \times 10^3$ |
| Diisopropyl adipate | $159 \times 10^3$ | $141 \times 10^3$ | $108 \times 10^3$ |
| Polyglycerol | $128 \times 10^3$ | $144 \times 10^3$ | $140 \times 10^3$ |
| Untreated | $125 \times 10^3$ | $156 \times 10^3$ | $103 \times 10^3$ |

Table 3 shows that when only the emollient was included, there was no bactericidal effect at all.

EXAMPLE 6

A series of aqueous sample solutions containing one of the 12 kinds of dialkyl adipate listed as Nos. 1–12 in Table 4 as the emollient was prepared according to formula A below. These sample solutions were used to examine the effects of the emollients on the bactericidal activity of chlorhexidine digluconate by the method for evaluation of bactericidal activity described below. The results are given in Table 4. Table 4 and the following Tables 5–9 show the number of viable bacteria as cells/500 μl, on the logarithmic scale Formula A

| | |
|---|---|
| Chlorhexidine digluconate | 0.2% (wt/v) |
| Emollient | 0.2% (wt/v) |
| Ethanol | 80% (v/v) |
| Deionized water | to make 100% |

Method for evaluation of bactericidal effect

A glass cylinder (diameter, 25 mm; height, 65 mm) was placed in the bottom of a 100-ml beaker, and chromatography paper (Toyo Roshi No. 50; 20×25 mm) was placed on the upper end of the cylinder Then 50 μl of one of the sample solutions listed above was dropped onto the center of the paper; the beaker was covered with a glass lid (diameter, 75 mm) and the paper was allowed to dry for 2 hours. Then, 10 μl of a suspension of *Staphylococcus aureus* ATCC No. 25923 that had been cultured in nutrient broth for 16 hours at 37° C. was dropped onto the area of the dried sample in the middle of the filter paper. The beaker was covered and was allowed to stand at room temperature so that the suspension would dry for 1 minute. The process of dropping and drying of the suspension of *S. aureus* was repeated for a total of 5 times. The filter paper was placed in a bottle that contained 20 g of sterilized glass beads (bead diameter, 3 mm) and 50 ml of sampling solution. The bottle was shaken vigorously for 45 seconds. The number of viable bacteria in this sampling solution was measured by the agar dilution method. The sampling solution used was a 0.3% aqueous solution of cocamide ether sulfate. The experiments with the samples containing different emollients, the sample containing serum, and the control sample not containing emollients were repeated for a total of three times for each sample. Measurement was also done of filter paper that was not treated by drops of the sample solutions. Enhancement of the bactericidal effect of the emollient was examined as follows: Logarithms of the number of viable bacteria in 500 µl of a sample of bacterial collection fluid containing a certain amount of emollient and a bacterial collection fluid containing no emollient was calculated and the values obtained were studied by variance analysis, the results of which were evaluated in the following way: ⊙ ; enhancement of the bactericidal effect by the emollient was significant at $p<0.01$; ○ enhancement of the bactericidal effect by the emollient was significant with p in the range of 0.01 to 0.05; X; enhancement of the bactericidal effect by the emollient was not found.

TABLE 4

| Emollient | Number of viable bacteria *a | Bactericidal effect |
|---|---|---|
| (1) Dimethyl adipate | 5.25 ± 0.09 | X |
| (2) Diethyl adipate | 5.21 ± 0.09 | X |
| (3) Diisopropyl adipate | 5.35 ± 0.09 | X |
| (4) Dipropyl adipate | 5.21 ± 0.09 | X |
| (5) Diisobutyl adipate | 4.80 ± 0.09 | ⊙ |
| (6) Dibutyl adipate | 4.79 ± 0.09 | ⊙ |
| (7) Di-tert-butyl adipate | 4.97 ± 0.09 | ⊙ |
| (8) Diisoamyl adipate | 4.92 ± 0.09 | ⊙ |
| (9) 2-Ethylbutyl adipate | 4.87 ± 0.09 | ○ |
| (10) Dihexyl adipate | 4.90 ± 0.09 | ○ |
| (11) Di-(2-ethylhexyl) adipate | 5.24 ± 0.09 | X |
| (12) Diisodecyl adipate | 5.30 ± 0.09 | X |
| (13) Control (no emollient) | 5.30 ± 0.09 | — |
| (14) Untreated | 5.40 ± 0.09 | — |

*a: The number is a scale of logarithms

Table 4 shows that the dialkyl adipates (emollients No. 5-10) with alkyl groups having 4-6 carbon atoms enhanced the bactericidal activity of chlorhexidine digluconate ($p<0.01$).

EXAMPLE 7

A series of sample solutions each containing one of the 12 kinds of dialkyl adipates used in Example 1 as the emollient and benzalkonium chloride as the bactericidal agent instead of chlorhexidine digluconate was prepared according to formula B below. These sample solutions were used to evaluate the effects of the emollients on the bactericidal activity of benzalkonium chloride by the same method as in Example 6 and by the method to evaluate bactericidal effects. The results are shown in Table 5.

Formula B

| | |
|---|---|
| Benzalkonium chloride | 0.2% (wt/v) |
| Emollient | 0.2% (wt/v) |
| Ethanol | 80% (v/v) |
| Deionized water | to make 100% |

TABLE 5

| Emollient | Number of viable bacteria *a | Bactericidal effect |
|---|---|---|
| (1) Dimethyl adipate | 4.71 ± 0.31 | X |
| (2) Diethyl adipate | 4.61 ± 0.31 | X |
| (3) Diisopropyl adipate | 4.19 ± 0.31 | X |
| (4) Dipropyl adipate | 4.40 ± 0.31 | X |
| (5) Diisobutyl adipate | 2.98 ± 0.31 | ⊙ |
| (6) Dibutyl adipate | 2.91 ± 0.31 | ⊙ |
| (7) Di-tert-butyl adipate | 3.28 ± 0.31 | ⊙ |
| (8) Diisoamyl adipate | 2.91 ± 0.31 | ⊙ |
| (9) 2-Ethylbutyl adipate | 3.44 ± 0.31 | ⊙ |
| (10) Dihexyl adipate | 3.58 ± 0.31 | ⊙ |
| (11) Di-(2-ethylhexyl) adipate | 4.46 ± 0.31 | X |
| (12) Diisodecyl adipate | 4.52 ± 0.31 | X |
| (13) Control (no emollient) | 4.62 ± 0.31 | |
| (14) Untreated | 5.19 ± 0.31 | |

*a: The number is a scale of logarithms

Table 5 shows that the dialkyl adipates (emollients Nos. 5-10) with alkyl groups having 4-6 carbon atoms significantly enhanced the bactericidal activity of the benzalkonium chloride ($p<0.01$). Thus, these emollients enhanced the bactericidal effects of benzalkonium chloride as they enhanced the bactericidal effects of chlorhexidine digluconate.

EXAMPLE 8

A series of sample solutions each containing one of 7 kinds of dibutyl esters of dibasic acids (Nos. 1-7 of Table 3) as the emollient was prepared according to formula A. These sample solutions were used to evaluate the effects of the emollients on the bactericidal activity of chlorhexidine digluconate by the same method as in Example 6. The results are shown in Table 6.

TABLE 6

| Emollient | Number of viable bacteria *a | Bactericidal effect |
|---|---|---|
| (1) Dibutyl oxalate | 5.31 ± 0.11 | X |
| (2) Dibutyl malonate | 5.12 ± 0.11 | X |
| (3) Dibutyl succinate | 5.04 ± 0.11 | ○ |
| (4) Dibutyl glutarate | 4.81 ± 0.11 | ⊙ |
| (5) Dibutyl adipate | 4.75 ± 0.11 | ⊙ |
| (6) Dibutyl suberate | 4.82 ± 0.11 | ⊙ |
| (7) Dibutyl sebacate | 4.86 ± 0.11 | ⊙ |
| (8) Control | 5.21 ± 0.11 | — |
| (9) Untreated | 5.48 ± 0.11 | — |

*a: The number is a scale of logarithms

Table 6 shows that dibutyl esters of dibasic acid (emollients Nos. 3-7) with polymethylene groups ($R^7$ in formula IV) having 2-8 carbon atoms enhanced the bactericidal activity of chlorhexidine digluconate.

EXAMPLE 9

A total of 11 emollients, six diesters of phthalic acid (Nos. 1-6 of Table 7), two triesters of citric acid (Nos. 7 and 8 of Table 7), and three triesters of phosphoric acid (Nos. 9-11 of Table 7), were selected, and a series of sample solutions were prepared according to formula A. These sample solutions were used to evaluate the effects of the emollients on the bactericidal activity of chlorhexidine digluconate by the same method as in Example 6. The results are shown in Table 7.

TABLE 7

| Emollient | Number of viable bacteria *a | Bactericidal effect |
| --- | --- | --- |
| (1) Dimethyl phthalate | 5.06 ± 0.08 | X |
| (2) Diethyl phthalate | 5.02 ± 0.08 | X |
| (3) Dibutyl phthalate | 4.59 ± 0.08 | O |
| (4) Diisobutyl phthalate | 4.56 ± 0.08 | O |
| (5) Di-(2-ethylhexyl)phthalate | 5.11 ± 0.08 | X |
| (6) Diisodecyl phthalate | 5.09 ± 0.08 | X |
| (7) Triethyl citrate | 5.11 ± 0.08 | X |
| (8) Tributyl citrate | 4.86 ± 0.08 | O |
| (9) Tricresyl phosphate | 4.99 ± 0.08 | X |
| (10) Triethyl phosphate | 5.03 ± 0.08 | X |
| (11) Tributyl phosphate | 4.66 ± 0.08 | |
| (12) Control | 5.05 ± 0.08 | — |

*a: The number is a scale of logarithms

Table 7 shows that dibutyl phthalate, diisobutyl phthalate, tributyl citrate, and tributyl phosphate, which are among the emollients of the composition of this invention, enhance the bactericidal activity of chlorhexidine digluconate.

EXAMPLE 10

A series of sample solutions each containing one of six diesters of phthalic acid (Nos. 1-6 of Table 8) or one of two triesters of citric acid (Nos. 7 and 8 of Table 8) was prepared according to formula B of Example 7. These sample solutions were used to evaluate the effects of the emollients on the bactericidal activity of chlorhexidine digluconate by the same method as in Example 6. The results are shown in Table 8.

TABLE 8

| Emollient | Number of viable bacteria *a | Bactericidal effect |
| --- | --- | --- |
| (1) Dimethyl phthalate | 5.19 ± 0.16 | X |
| (2) Diethyl phthalate | 4.98 ± 0.16 | X |
| (3) Dibutyl phthalate | 3.71 ± 0.16 | O |
| (4) Diisobutyl phthalate | 3.67 ± 0.16 | O |
| (5) Di-(2-ethylhexyl)phthalate | 5.25 ± 0.16 | X |
| (6) Diisodecyl phthalate | 5.34 ± 0.16 | X |
| (7) Triethyl citrate | 5.13 ± 0.16 | X |
| (8) Tributyl citrate | 4.49 ± 0.16 | |
| (12) Control | 5.09 ± 0.16 | — |

*a: The number is a scale of logarithms

Table 8 shows that the dibutyl phthalate, diisobutyl phthalate, and tributyl citrate, which are among the emollients of the composition of this invention enhance the bactericidal activity of chlorhexidine digluconate.

EXAMPLE 11

A series of sample solutions were prepared according to formula C with the use of 12 bactericidal agents (Nos. 1-12 of Table 9) that are widely used in the medical field as bactericides, and with diisobutyl adipate as the emollient. Separately, sample solutions that did not contain diisobutyl adipate were prepared. The sample solutions were used to evaluate the effects of the emollients on the bactericidal activity of the bactericidal agents by the same method as in Example 6. The results are shown in Table 9. The values in Table 9 were evaluated by the t-test.

Formula C

| Bactericidal agent | 0.2% (wt/v) |
| --- | --- |
| Diisobutyl adipate | 0.2% (wt/v) |
| Ethanol | 80% (v/v) |
| Deionized water | to make 100% |

TABLE 9

| Bactericidal agent | Number of viable bacteria *a | | Bactericidal effect |
| --- | --- | --- | --- |
| | Diisobutyl adipate absent | Diisobutyl adipate present | |
| (1) Benzalkonium chloride | 5.04 ± 0.05 | 4.20 ± 0.21 | O |
| (2) Benzethonium chloride | 4.70 ± 0.03 | 1.84 ± 0.33 | O |
| (3) Cetylpyridinium chloride | 4.27 ± 0.30 | 2.53 ± 0.07 | O |
| (4) Didecyl dimethyl ammonium chloride | 2.02 ± 0.05 | 0 | O |
| (5) Chlorhexidine digluconate | 5.15 ± 0.08 | 4.39 ± 0.11 | O |
| (6) Polyhexamethylene biguanidine | 5.05 ± 0.05 | 4.91 ± 0.10 | X |
| (7) Povidone-iodine | 5.28 ± 0.08 | 5.26 ± 0.04 | X |
| (8) Phenol | 5.39 ± 0.04 | 5.38 ± 0.06 | X |
| (9) Triclosan | 1.59 ± 0.10 | 5.22 ± 0.07 | X |
| (10) Isopropylmethylphenol | 5.33 ± 0.14 | 5.36 ± 0.05 | X |
| (11) Trichlorocarbanilide | 5.39 ± 0.06 | 5.32 ± 0.06 | X |
| (12) Sodium alkyldiamino-ethylglycine | 5.34 ± 0.03 | 5.31 ± 0.04 | X |

*a: The number is a scale of logarithms

Table 9 shows that the combined use of a bactericidal agent selected from the group of benzalkonium chloride, benzethonium chloride, cetylpyridinium chloride, and chlorhexidine digluconate together with the emollient diisobutyl adipate, gave more effective bactericidal effects compared to the use of the bactericidal agents alone.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty that reside in the present invention, including all features that would be treated as equivalents thereof by those skilled in the art to which this invention pertains.

What is claimed is:

1. A disinfectant composition for medical use comprising ethanol used for disinfection, a bactericidal agent, and an emollient, wherein
   said bactericidal agent is chlorhexidine digluconate;
   said emollient is selected from the group consisting of diesters of dibasic acid of the formula (IV), triesters of citric acid of the formula (V), triesters of phosphoric acid of the formula (VI);
   said ethanol used for disinfection is an aqueous solution of ethanol ranging in concentration from 50 to 95% (v/v), said bactericidal agent is contained at a concentration of from 0.01 to 0.5% (wt/v), and said emollient is contained at a concentration of from 0.1 to 1.0% (wt/v):

(IV)

wherein R⁶ is alkyl containing 4 to 6 carbon atoms, and R⁷ is phyenylene or polymethylene of the formula —(CH$_2$)$_n$—, said n being an integer of from 2 to 8;

(V)

wherein R⁸ is alkyl containing 4 to 6 carbon atoms;

(VI)

wherein R⁹ is alkyl containing 4 to 6 carbon atoms.

2. A disinfectant composition for medical use comprising ethanol used for disinfection, a bactericidal agent, and an emollient, wherein
said bactericidal agent is benzalkonium chloride;
said emollient is selected from the group consisting of diesters of dibasic acid of the formula (IV), triesters of citric acid of the formula (V), triesters of phosphoric acid of the formula (VI);
said ethanol used for disinfection is an aqueous solution of ethanol ranging in concentration from 50 to 95% (v/v), said bactericidal agent is contained at a concentration of from 0.01 to 0.5% (wt/v), and said emollient is contained at a concentration of from 0.1 to 1.0% (wt/v):

(IV)

wherein R⁶ is alkyl containing 4 to 6 carbon atoms, and R⁷ is phenylene or polymethylene of the formula —(CH$_2$)$_n$—, said n being an integer of from 2 to 8;

(V)

wherein R⁸ is alkyl containing 4 to 6 carbon atoms;

(VI)

wherein R⁹ is alkyl containing 4 to 6 carbon atoms.

* * * * *